United States Patent
Heilmann et al.

[11] Patent Number: 5,928,744
[45] Date of Patent: Jul. 27, 1999

[54] PVC-FREE MULTILAYER TUBE FOR MEDICAL PURPOSES, PROCESS FOR THE PRODUCTION THEREOF AND USE

[75] Inventors: Klaus Heilmann, Wendel, Germany; Thomas Nicola, Spicheren, France

[73] Assignee: Fresenius AG, Germany

[21] Appl. No.: 08/689,862

[22] Filed: Aug. 15, 1996

[30] Foreign Application Priority Data

Sep. 16, 1995 [DE] Germany .......................... 195 34 455

[51] Int. Cl.$^6$ .................................................. F16L 11/04
[52] U.S. Cl. .................. 428/36.6; 428/36.7; 428/36.91; 428/423.1; 428/483; 428/518; 428/520; 138/137; 604/403
[58] Field of Search .................................. 428/35.2, 35.4, 428/35.7, 36.9, 36.91, 36.6, 36.7, 332, 516, 517, 518, 519, 423.1, 483, 520; 604/8, 403, 408; 128/DIG. 24; 138/137, 141

[56] References Cited

U.S. PATENT DOCUMENTS

| | | | |
|---|---|---|---|
| 4,516,977 | 5/1985 | Herbert | 604/403 |
| 4,857,409 | 8/1989 | Hazelton et al. | 428/35.2 |
| 4,929,479 | 5/1990 | Kihachi et al. | 428/35.2 |
| 4,948,643 | 8/1990 | Mueller | 428/36.6 |
| 5,520,975 | 5/1996 | Fujio et al. | 428/35.9 |
| 5,529,821 | 6/1996 | Ishikawa et al. | 428/36.91 |
| 5,562,127 | 10/1996 | Fanselow et al. | 428/137 |
| 5,601,889 | 2/1997 | Chundury et al. | 428/35.2 |

FOREIGN PATENT DOCUMENTS

| | | |
|---|---|---|
| 0 533 493 | 3/1993 | European Pat. Off. . |
| 0 564 206 | 10/1993 | European Pat. Off. . |
| 0 738 589 | 10/1996 | European Pat. Off. . |
| 0 739 713 | 10/1996 | European Pat. Off. . |
| 42 19 071 A1 | 6/1992 | Germany . |
| 44 04 041 C1 | 2/1994 | Germany . |
| 195 34 455 | 4/1996 | Germany . |
| PCT/US93/04568 | 5/1993 | WIPO . |

*Primary Examiner*—Rena L. Dye
*Attorney, Agent, or Firm*—Fulbright & Jaworski L.L.P.

[57] ABSTRACT

According to the invention, strong adhesion of the layers to each other and simple formation of a strong and leakproof connection with bags or connectors made from polypropylene or polycarbonate during steam sterilisation is achieved by the first plastic material containing at least one polymer which is dimensionally stable at temperatures of $\geq 121°$ C., while the second plastic material contains at least one polymer which is no longer dimensionally stable at temperatures of $\geq 121°$ C. A layer C) (2) is optionally present, the plastic material of which contains at least one polymer which is dimensionally stable at temperatures of $\geq 121°$ C. The invention can be used for medical purposes, in particular as a fluid line in dialysis, infusion or artificial feeding, primarily in connection with connectors or medical bags.

21 Claims, 1 Drawing Sheet

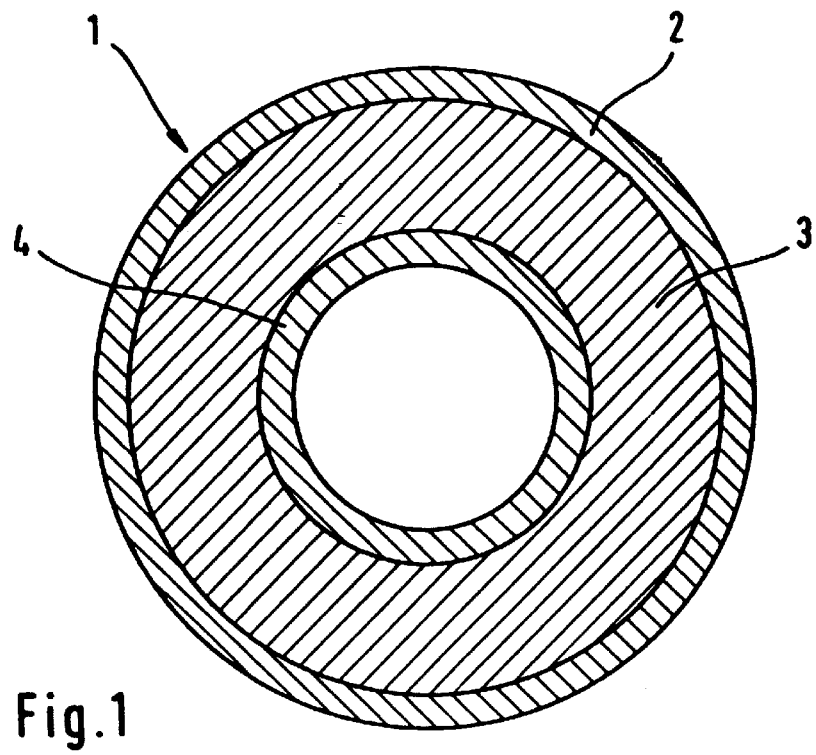
Fig.1
Fig. 2
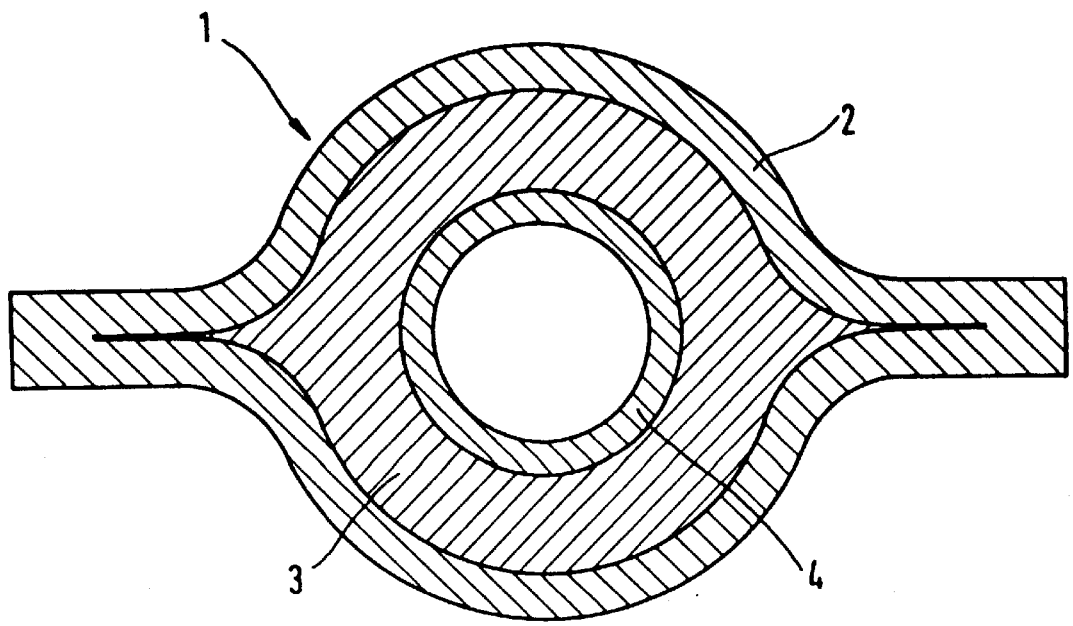

PVC-FREE MULTILAYER TUBE FOR MEDICAL PURPOSES, PROCESS FOR THE PRODUCTION THEREOF AND USE

BACKGROUND OF THE INVENTION

1. Field of the Invention

This invention relates to a PVC-free multilayer tube for medical purposes according to the pre-characterising clause of claim 1, to a process for the production of such PVC-free multilayer tubes according to the pre-characterising clause of claim 18 and to the use of the PVC-free multilayer films according to the invention.

2. Description of the Prior Art

The following have been cited as prior art
WO-A-92/11820 (=D1),
DE-A-28 31 034 (=D2),
U.S. Pat. No. 4,948,643 (=D3),
EP-A-0 136 848 (=D4),
DE-PS-44 04 041 (=D5),
DE-OS-42 19 071 (=D6),
DE-OS-39 14 998 (=D7) and
WO-A-93/23093 (=D8).

PVC-free materials=non-PVC materials and single-layer tubes produced therefrom having only one layer are known, for example, from D1. This document proposes a tube material for medical purposes which contains a blend of polyurethane and polyester and which may be subjected to sterilisation in an autoclave, is heat-sealable and is sealable and fusible with high frequency energy. The described tube material is free of the PVC plasticiser DEHP, a phthalate which is suspected of having carcinogenic characteristics. It does, however, optionally contain as plasticiser certain additional amounts of a citric acid ester (butyryltrihexyl citrate) and further processing auxiliaries such as internal or external lubricants. While the thermoplastic plastic material disclosed in D1 may be processed by known shaping processes such as extrusion, injection moulding or blow moulding, it is essentially intended for use in medical bags or connectors made from PVC. It is only with these "conventional" PVC materials that it exhibits satisfactory compatibility, in particular for joining by heat or high frequency sealing.

D2 discloses PVC-free plastic compositions which are suitable for the production of tubes to receive or convey blood or medical solutions. D2 in particular provides plastic compositions which consist of 10 to 40 wt. % of a polyolefin substantially consisting of propylene units, 40 to 85 wt. % of a block copolymer prepared from a central polyethylene or polybutylene block with terminal polystyrene blocks, 10 to 40 wt. % of a polymeric plasticiser based on polyethylene and optionally an anti-oxidant. While the materials disclosed are indeed flexible, thoroughly heat resistant, have the softness required for medical applications and are very largely capable of solving the ageing problems caused by low molecular weight plasticisers, the stability and stiffness of the material still leaves something to be desired. In the stated single-layer material, any increase in stiffness by increasing the proportion of polypropylene would in particular result in a reduction in the softness and flexibility of the finished tube or bag.

D3 provides multilayer tubes for medical connection lines. Three-layer tubes are shown, the outer layer of which is based on ethylene vinyl acetate (EVA) and the inner layer on polyvinyl chloride (PVC). Since adhesion between the inner and outer layers is deficient, a coupling agent layer made from an ethylene-based polymer containing vinyl acetates and acrylates, is coextruded with the other two materials as a central layer. Plastic materials having the stated sequence of layers are in particular suitable for use as junction and connection pieces or tubes for medical bags made from EVA (compatibility of the outer layer with the bag) and allow a PVC membrane tube to be introduced and securely attached within the junction piece or tube, for example by solvent bonding. The multilayer tubes shown in D3 are highly questionable from a medical point of view as the PVC layer contains considerable quantities of trimellitic acid esters as the plasticiser and these compounds may be carcinogenic.

D4 finally discloses multilayer tubes which may be considered as a potential replacement for PVC tubes in the medical sector. However, D4 does not completely exclude the use of PVC, indeed it is entirely tolerated as a material or blend component for an interlayer or the inner layer.

D4 specifically relates to a three-layer tube for medical purposes, the inner layer of which consists of an ethylene/propylene copolymer, a polypropylene, a copolyester prepared from a polyether and a polyethylene terephthalate, polyurethane, polyvinyl chloride or a blend of copolyester and ethylene/vinyl acetate copolymer.

The interlayer may consist of LLDPE (linear low density polyethylene), ethylene/vinyl acetate copolymer (EVAC), modified EVAC, ethylene/methyl acrylate copolymer (EMAC), modified EMAC, PVC or a blend of the above-stated compounds.

The outer layer according to D4 is formed from polypropylene, ethylene/propylene copolymer or modified ethylene/propylene copolymer.

Selection of the materials for the interlayer is substantially determined by the ability of these materials to impart the necessary flexibility to the complete multilayer tube structure. The criterion for selection of the inner layer material is sufficient heat resistance to render the resultant tube autoclavable, while selection of an outer layer material is substantially guided by the desire to allow relatively resistant ultrasound, heat or high frequency energy sealing with a polycarbonate connector.

Apart from the fact that the tubes according to D4 do not completely exclude the use of PVC, and while the tubes are indeed compatible with polycarbonate, they are less suited to forming a bond with other newer and more advantageous polypropylene-based bag or connector materials.

Moreover, the flexible central layer according to D4 is usually the thickest layer, which often entails inadequate stiffness of the complete tube. It is thus generally and not only optionally necessary to irradiate the extruded tubes in order to achieve high temperature sterilisability by means of radiation-induced crosslinking. This operation is elaborate.

D5 relates to a polymer material for medical instruments. Silane-grafted VLDPE's or ULDPE's are disclosed which have been crosslinked with moisture in order to obtain, for example, transparent, kink-resistant and sterilisable tubes, in particular by extrusion. Elevated degrees of crosslinking are a prerequisite for steam sterilisability of the finished product. Although the material is apparently suitable as a replacement for PVC, the resultant single-layer tubes are not capable forming a good and direct bond with an insert during simple high temperature sterilisation without losing dimensional stability.

D6 discloses radiation-sterilisable recyclable infusion and transfusion sets, in which all the components are produced from thermoplastic or elastomeric homopolymers, copolymers, block copolymers based on polyolefins. D6 in particular publically discloses connection tubes made from PE-LLD or from linear PE-LVLD, but does not exclude the use of EVA or special ionomers.

These tubes are connected by using organic solvents such as cyclohexane. Alternatively, the tubes may be welded by ultrasound or bonded with light- or UV-curable adhesives.

D7 relates to transfer systems for infusion of transfusion purposes, in which, in order to ensure environmentally sensitive recycling, all components consist of a single polymer, copolymer or block copolymer without using PVC. The polymeric materials used are based on styrene polymers.

D8 relates to PVC-free coextruded multilayer tubes for medical purposes which have a core layer consisting of a blend of polyamide and EVA. An outer layer is applied onto this inner core layer by means of a coupling layer. The coupling layer essentially contains copolyester and SEBS copolymer, optionally PP and EVA. Selection of the materials proves that the disclosed tube must have the disadvantages associated with the use of EVA, copolyester or polyamide.

SUMMARY OF THE INVENTION

In the light of the disadvantages associated with the embodiments described in the cited prior art, the object of the present invention is to provide a tube for medical purposes which may individually be tailored to many different connector and bag materials, in particular those based on polypropylene or polycarbonate. It is moreover desirable for a solid bond to be achievable with the novel tube material without additional coupling agents or the like. The novel multilayer tube should additionally be sufficiently flexible, elastic and soft while nevertheless being as resistant as possible to kinking, relatively dimensionally rigid and thermally stable. Finally, when in contact with the fluids conventional in medicine, the tube should also not release any hazardous substances into these fluids and should in particular be inert towards medical solutions. An object of the invention is moreover to state a process for the production of such a multilayer tube. A further object of the invention is to indicate possible applications for the tube material according to the invention.

These and other objects not stated in greater detail are achieved by a PVC-free multilayer tube for medical purposes of the above-stated type having the features of the characterising clause of claim 1. Particular developments are protected in the dependent claims of claim 1. The object of the invention is achieved with regard to the process by a process according to claim 18, while claims 26 and 28 protect the use of the PVC-free multilayer tube according to the invention.

Because a PVC-free multilayer tube for medical purposes with at least two layers, of which a base layer A) of a first plastic material is bonded with at least one connection layer B) of a second plastic material, the first material contains at least one polymer which withstands high temperature sterilisation at $\geq 121°$ C. without deformation, has a Shore D of $\geq 32$, which has a residual stress at $\geq 121°$ C. which is sufficient to form a press fit on a connection point, and from which a ring or loop of a diameter of down to 60 mm may be formed without kinking, while the second material contains at least one polymer which during high temperature sterilisation at 121° C. has a tendency to flow under the connection pressure arising during formation of a press fit and has a Shore A hardness of $\leq 65$, such that the first plastic material is dimensionally stable at temperatures of $\geq 121°$ C. and the second plastic material is no longer dimensionally stable, it is possible to provide a flexible tube which is transparent on completion of high temperature sterilisation, which has sufficient kink resistance and may be closed with tube clamps or the like. The PVC-free multilayer tube according to the invention is additionally able to form a strong and leakproof connection with a medical bag or connector, in an exceptionally simple manner during a possible high temperature sterilisation.

The present invention is based inter alia on the concept of adapting various plastic layers relative to each other in a multilayer tube material in such a manner that at least one layer, acting as the base layer, imparts sufficient thermal stability to the tube material, while at least one other layer, acting as a connection or joining layer, ensures the formation of a strong and leakproof connection with a bag, connection port, connector or another tube without it being necessary to use additional adhesive, sealant or sealing compositions or auxiliary substances or to use other sealing methods (high frequency energy or the like).

For the purposes of the invention, "sterilisation" is generally taken to mean a process for killing or inactivating (viruses) all microorganisms, including the highly resistant dormant forms, wherein the tubes according to the invention should in particular withstand steam sterilisation in autoclaves with pressurised steam of at least 121° C., corresponding to a pressure of approximately one atmosphere above atmospheric, so-called autoclaving or autoclave treatment, without suffering damage.

For the purposes of the invention, "plastic material" is furthermore taken to mean those materials substantially consisting of macromolecular organic compounds, wherein the plastic materials are also known as polymers, in particular including homopolymers and copolymers (random, block and/or graft polymers) and mixtures (=blends) of the above-stated substances.

Dimensional stability during high temperature sterilisation is one important criterion for the selection and incorporation of a polymer into a plastic material and thus into a certain functional layer of the multilayer PVC-free tube for medical purposes.

A plastic material is deemed to be dimensionally stable in this connection if a tube specimen of at least 10 mm in length, an internal diameter of 5 mm and an external diameter of 7 mm withstands hot steam sterilisation at 121° C. with a heating time of at least 15 minutes, holding time of at least 15 minutes and cooling time of at least 10 minutes without visible dimensional change, such as "collapse" or "ovality".

The temperature relevant for the softening of the polymers or plastic materials according to the invention is the steam sterilisation temperature, namely 121° C. Since the base layer contains a polymer having dimensional stability and thus heat resistance with regard to deformation even at temperatures in excess of 121° C., the possibility of free-flowing softening or reaching the liquid state of the base layer during steam sterilisation is very largely excluded, while a polymer of the plastic material of the connection layer, which reaches free-flowing softening under compressive pressure at 121° C., allows softening of the connection layer under standard steam sterilisation conditions. As a consequence, a bond may be formed at a point of contact with a connecting element without the shape of the tube changing uncontrollably.

The stated temperatures relate in each case to the pressure during steam sterilisation, i.e. approximately 1 atmosphere above atmospheric. It will, however, be understood that the pressure dependency of softening temperature over the range between standard pressure and the pressure above atmospheric required for steam sterilisation is generally negligibly small.

Depending upon the desired function of the PVC-free tube according to the invention, it may be advantageous to arrange the special layer B) capable of forming a connection on the outside, inside or both outside and inside. The PVC-free multilayer tube of the invention is accordingly preferably characterised by the sequence of layers B) A), A) B) or B) A) B), in each case from the inside outwards.

In the first case, the tube according to the invention may, for example, be "plugged" onto a connector made of a suitable material, such that the inner layer of the tube is in contact with the outer surface of the connector. In the second case, the tube according to the invention is intended for insertion into a hollow article, the inner surface of which is made from a material suitable for forming a connection, while both connection options are alternatively or simultaneously possible when two connection layers (outside and inside) are arranged in the PVC-free multilayer tube according to the invention. In the event of a connection with a connector, the connection layer is preferably on the inside, while in the event of a connection with, for example, a bag, the connection layer is preferably on the outside.

In addition to the hitherto described base and connection layers, in a preferred development, the PVC-free multilayer tube of the invention has a further functional layer, namely at least one additional transparent cover layer C) as an outer layer made from a third plastic material, wherein a layer C) may be arranged as the innermost or outermost layer.

The cover layer imparts an improved surface finish to the multilayer tube with regard to tackiness, dullness and reduced coefficient of friction, transparency and specific sealing characteristics. Layer C) may in principle be provided as a final layer either on the inside or on the outside. It is, however, preferred for the purposes of the invention that, in the event that the outermost or innermost outer layer is a connection layer B), the corresponding opposite outer layer is a layer C).

In a particularly advantageous development, at least the cover layer is arranged to form a lipped tube (FIG. 2). Accordingly, embodiments of such PVC-free multilayer tubes which are particularly preferred according to the invention are those characterised by the sequence of layers B) A) C)/C) A) B)/C) B) A) B) or B) A) B) C), in each case from the inside outwards. Depending upon the use of the tube, the inner layer must be compatible with the solution flowing through the tube.

In order to ensure the above-mentioned characteristics of the layer C), in a further advantageous embodiment the cover layer C) consists of a third plastic material which contains at least one polymer having heat resistance to deformation of >121° C.

In preferred PVC-free multilayer tubes according to the invention, the first plastic material for the base layer predominantly comprises a synthetic, isoprene-based rubber or polypropylene having a density $\rho$ of $\leq 0.9$ g/cm³ and the second plastic material for the connection layer predominantly comprises a polyethylene copolymer or a synthetic rubber having an $\overline{M}_w$ of <100000 g/mol. This combination for each base layer A) and the connection layer or layers B) is capable of fulfilling many required characteristics. The following polymers are particularly advantageously used for the purposes of the invention. Percentages are weight percentages.

| Cover layer: | Thickness = 10–50 μm |
|---|---|
| 40%–60% PP-R | (PP23M 10 cs 264, REXENE) and |
| 60%–40% SIS | (HVS 3, Kuraray) ; or Tuftec H 1052 (Asahi) |
| Base layer: | Thickness: 900–980 μm at a tube wall thickness of approx. 1 mm |
| 50–100% SIS | (HVS/3, Kuraray) and |
| 50–0% PP-R | (PP 23M10cs264, REXENE) ; |
| | - PP having Shore D $\leq$ 32, $\rho$ = 0.9 g/cm³; |
| | (for example Adflex 100 G, Himont, having a rubber content of up to 50%, for example PIB, styrene/ethylene/butylene rubber, styrene/ethylene/propylene rubber, SIS) |
| Connection layer: | Thickness 10–50 μm |
| 100% SEBS compound | (PR 3415, Wittenburg) |
| 100% SEPS | (Septon 2277, Kuraray) or |
| 50–100% PE-copolymer | (Engage XU58.000 52, DOW) and |
| 0–50% SEBS/SEB | (Kraton G 1726, Shell) ; |

Key to abbreviations:
PP-R = polypropylene random copolymer
SIS = styrene/isoprene/styrene
SEBS = styrene/ethylene/butylene/styrene rubber
SEB = styrene/ethylene/butylene rubber
SEPS = styrene/ethylene/propylene/styrene rubber
PE-copolymer = polyethylene copolymer It may be stated with regard to adhesion between layers made from materials A), B) and C) that this characteristic is in principle adequate. Adhesion may, however, advantageously be increased by layers A), B) and/or C) each additionally containing up to 40 wt. %, relative to 100 wt. % of their composition as-described and defined above, of the plastic material which serves to form one or both of the adjacent layers of the PVC-free multilayer tube. A further interlayer made from the polymer materials of the adjacent layers is also advantageous.

This material "mediation" or replacement of material distinctly increases the mutual compatibility of the layers formed together in a tube without compromising the other characteristics.

Another essential and particularly preferred feature of the invention is that in a development of the PVC-free multilayer tube according to the invention the plastic materials for all the layers of the tube are selected in such a manner that they substantially consist of polyolefin homopolymers or polyolefin copolymers or modifications thereof (for example SEBS). It was particularly surprising that the invention for the first time makes it possible to create a PVC-free multilayer tube consisting exclusively of environmentally compatible materials which allow the straightforward formation of a connection with connectors during steam sterilisation and simultaneously fulfil all the requirements for a tube usable in medical applications.

With regards to geometry, the tubes themselves may be produced in any required and conventional thicknesses and sizes. The PVC-free multilayer tube according to the invention preferably consists of more than 96–98 vol. %, relative to the entire volume of the tube material, of the base layer A). The individual layers themselves are preferably of the following thicknesses: base layer A) thickness of >900 μm, connection layer B) thickness of between 10 μm and 50 μm and sealing layer C) thickness of between 10 μm and 50 μm.

The present invention also provides a process for the production of a PVC-free multilayer tube for medical purposes, in which, in order to produce a plastic multilayer film having at least two layers, a first plastic material to form a base layer A) and a second plastic material to form at least one connection layer bonded thereto are coextruded together and shaped into a substantially coaxial and cylindrical multilayer tube, wherein the process is characterised in that a first plastic material is used which withstands high temperature sterilisation at ≧121° C. without deformation, has a Shore D hardness of ≦32, which has a residual stress at ≧121° C. which is sufficient to form a press fit on a connection point, and from which a ring or loop of a diameter of down to 60 mm may be formed without kinking, while a second plastic material is used which contains at least one polymer which during high temperature sterilisation at 121° C. has a tendency to flow under the connection pressure arising during formation of a press fit and has a Shore A hardness of ≦65, such that the first plastic material is dimensionally stable at temperatures of ≧121° C. and the second plastic material is no longer dimensionally stable.

Shaping is performed using methods familiar to the person skilled in the art, such as for example vacuum sizing. It is particularly important for the purposes of the invention that it is possible by coextruding two or more layers together to combine two or more desired properties of individual components in a tube in order to improve the quality of the tube.

To this end, the coextrusion process makes it possible, with appropriate selection of the extrusion partners, to provide tailored PVC-free multilayer tubes, which uniquely allow coupling agents to be completely omitted while nevertheless influencing the required characteristics and additionally other important characteristics such as gas and water vapor permeability, material strength, weldability, transparency and heat resistance of the tube.

Selection of the layer materials to be coextruded together is of great significance to the invention, wherein plastic materials or layers are particularly preferably selected such that all the layers of the PVC-free multilayer tube substantially consist of polyolefin homopolymers and/or polyolefin copolymers, or of polymers based thereon, such as for example modifications of polyolefins (for example SEBS).

While the coextrusion of such materials is indeed known in principle, it could not be predicted on the basis of current experience that a multilayer tube of the complexity of the tube according to the invention could straightforwardly be produced. That this was possible according to the invention was particularly surprising as it has otherwise frequently been found in practice that even the use of sometimes tabulated polymer properties, such as data relating to composite adhesion, does not necessarily result in success. This means that achieving a stated object by merely making a selection from among known materials is not in principle straightforwardly possible for a multilayer coextruded tube. Adjusting melt viscosity when coextruding rubbers such as PIB with PP is particularly difficult.

It is furthermore preferred in the process according to the invention that, in order to shape a PVC-free multilayer tube, the plastic materials are selected such that all the layers of the tube additionally contain up to 40 wt. % of the material of the adjacent layer or layers. By this means, it is possible to a certain extent to offset low adhesion between two adjacent layers. After the actual shaping operation, the resultant tube may be further processed in a conventional manner. The tube is preferably quenched with water after shaping. Such quenching "freezes in" the amorphous state to achieve an optimum composite having elevated flexibility and adequate stiffness, but, above all, quenching the melt improves the transparency of the tube because crystalline zones cannot be formed. This results in a low degree of crystallinity and thus in elevated transparency and toughness.

The PVC-free multilayer tube according to the invention is outstandingly suitable for use in the medical sector. The materials of the multilayer tube are all selected such that the tube is transparent, kink-resistant and flexible, but in particular sterilisable at high temperatures and, due to the compressive force simultaneously exerted by the tube, a strong, bacteria-proof connection may be formed with an appropriate connector. The non-PVC multilayer film of the invention is moreover also biocompatible. The use of PVC, which always contains some plasticisers, is avoided and coupling agents, which could possibly diffuse through the layers of the plastic material, are likewise not required.

By virtue of its outstanding material characteristics and performance, the PVC-free multilayer tube according to the invention is particularly advantageously used as a fluid line in dialysis, infusion or artificial feeding. To this end, it is advantageous to provide a welding lip for connection to the supply bag at least in the area of the connection.

The compatibility of the connection layer material of the multilayer tube according to the invention with the connection pieces of medical bags (principally made from polypropylene) and/or specific connection methods conventionally used in medicine, for example in the form of polypropylene connectors, is of particular benefit in this connection. Connectors or bags may here be provided with a rough surface onto which a PVC-free multilayer tube according to the invention is placed, such that the inner surface of the PVC-free-multilayer tube with the connection layer B) of the tube forms a press fit with the rough outer surface of the connector or bag (optionally connection port of the bag).

Formation of a good and strong connection is ensured by the surface of the polypropylene parts and the flow characteristics of the connection layer B) of the tube under the action of heat, for example during steam sterilisation, since the connection layer material flows into the surface irregularities of the connector or bag connection port. The connection is still further improved if the plastic materials used to produce the connection layer B) of the tube are blended with a proportion of between 1 and 40 wt. %, relative to 100 wt. % of the material of the connection layer, of a plastic material from which the connector or connection port of the bag is made. Connection may be improved by roughening the surface.

Further advantages and particulars of the invention may be found in the Examples which are illustrated with reference to the attached figures.

BRIEF DESCRIPTION OF THE DRAWING

The figures show:

FIG. 1 is a cross-section through an embodiment according to the invention of the PVC-free multilayer tube, FIG. 2 is another embodiment with lips.

DESCRIPTION OF THE PREFERRED EMBODIMENT

The figures show a three-layer tube 1 according to the present invention. In the embodiment shown in FIG. 1, the outer layer 2 of the tube 1 is a cover layer C) made from a blend of SEBS compound, SEPS compound, a PP/SIS blend or PP/styrene/ethylene/butylene/(propylene) rubber blend, SEBS and/or SEPS.

As the base layer A), interlayer 3 constitutes the largest volume of the tube shell. Suitable materials include, inter alia, styrene/ethylene/butylene rubber with PP, PIP with PP, SEPS with PP, PP and SIS with PP.

The connection layer 4 consists of SEBS compound with SEBS/SEB (Kraton G 1726 and Kraton G 1652, Shell) and PE copolymer (Engage XU58000, 52 DOW) with SEBS/SEB (Kraton G 1726, Shell), SEPS/SEP (Septon 2277, Kuraray). SEBS (Kraton G 1726) is here a low molecular weight SEBS having a diblock content of at least 20%, while SEBS (Kraton G 1652) is a higher molecular weight SEBS having no appreciable diblock content.

Layers A), B) and C) exhibit the following values for dimensional stability, modulus of elasticity and hardness:

|  | Modulus of elasticity | Hardness | Dimensional stability in high temperature sterilisation |
|---|---|---|---|
| Main base layer A) | $\leq 80$ N/mm$^2$ | Shore D $\leq 32$ | > 123° C. |
| Connection layer B) | $\leq 80$ N/mm$^2$ | Shore A $\leq 65$ | < 121° C. |
| Cover layer C) | < 1000 N/mm$^2$ | < R90*⁾ | > 123° C. |

*⁾Means a Rockwell hardness value of 90; c.f. DIN 10109-1

Further advantages and embodiments may be found in the following patent claims.

We claim:

1. PVC-free multilayer tube for medical purposes having a first base layer A) of a first plastic material bonded to a second connection layer B) of a second plastic material, characterised in that the first plastic material contains at least one polymer, which withstands high temperature sterilisation at $\geq 121°$ C. without deformation, and has a Shore D hardness of $\leq 32$ having a residual stress at $\geq 121°$ C. sufficient to form a press fit on a connection point, while the second plastic material contains at least one polymer, which during high temperature sterilisation at approximately 121° C. or higher has a tendency to flow under the connection pressure arising during formation of the press fit, and has a Shore A hardness of $\leq 65$, such that the first plastic material is dimensionally stable at temperature of $\geq 121°$ C. and the second plastic material is no longer dimensionally stable at temperature of $\geq 121°$ C.

2. PVC-free multilayer tube according to claim 1, characterised in that polymers having dimensional stability of $\geq 121°$ C. form the predominant proportion of the mass of the first plastic material or polymers which lose their dimensional stability at 121° C. constitute the predominant proportion of the mass of the second plastic material.

3. PVC-free multilayer tube according to claim 1, characterised in that the first base layer A) is still dimensionally stable at temperature of $\geq 121°$ C. and the second connection layer B) is no longer dimensionally stable under connection pressure at a temperature of 121° C.

4. PVC-free multilayer tube according to claim 1, characterised by the sequence of layers B) A), A) B) or B) A) B), in each case from the inside outwards.

5. PVC-free multilayer tube according to claim 1, characterised in that the tube additionally has at least one transparent cover layer C) of a third plastic as the outer layer, wherein layer C) is arranged either as the innermost or outermost layer.

6. PVC-free multilayer tube according to claim 5, characterised in that the outermost or innermost outer layer is a second connection layer B) and the corresponding opposite outer layer is a cover layer C).

7. PVC-free multilayer tube according to claim 5, characterised by the sequence of layers B) A) C), C) A) B), C) B) A) B) or B) A) B) C), in each case from the inside outwards.

8. PVC-free multilayer tube according to claim 7, characterised by the layers B) A) C) or C) A) B), depending upon the use of the tube.

9. PVC-free multilayer tube according to claim 5, characterised in that the third plastic material contains at least one polymer which is dimensionally stable at temperatures of $\geq 121°$ C.

10. PVC-free multilayer tube according to claim 9, characterised in that the third plastic material exhibits dimensional stability at temperatures of $\geq 121°$ C.

11. PVC-free multilayer tube according to claim 5, characterised in that the layers adhere together without additional coupling agents.

12. PVC-free multilayer tube according to claim 5, characterised in that the layers are substantially free of plasticisers, antiblocking agents, antistatic agents and other fillers.

13. PVC-free multilayer tube according to claim 5, characterised in that layers A), B) or C) each additionally contain up to 40 wt. %, relative to 100 wt. % of the plastic material thereof, of the plastic material used to form one or both of the adjacent layers of the PVC-free multilayer tube.

14. PVC-free multilayer tube according to claim 5, characterised in that the plastic materials for all the layers of the tube are selected such that they substantially consist of polyolefin homopolymers or polyolefin copolymers.

15. PVC-free multilayer tube according to claim 5, characterised in that the first base layer A) is of a thickness of between 900 and 980 μm.

16. PVC-free multilayer tube according to claim 5, characterised in that the second connection layer B) is of a thickness of between 10 and 50 μm.

17. PVC-free multilayer tube according to claim 6, characterised in that the cover layer C) is of a thickness of between 10 and 50 μm.

18. A PVC-free multilayer tube according to claim 1, wherein the tube is used for medical purposes.

19. A PVC-free multilayer tube according to claim 18, wherein the tube is used as a fluid line in dialysis, infusion or artificial feeding.

20. A PVC-free multilayer tube according to claim 18, wherein the tube is used as a blood tube.

21. A PVC-free multilayer tube for medical purposes having at least two layers, of which a base layer A) of a first plastic material is bonded with at least one connection layer B) of a second plastic material, characterised in that the first plastic material contains at least one polymer which withstands high temperature sterilisation at $\geq 121°$ C. without deformation, has a Shore D hardness of $\leq 32$, which has a residual stress at $\geq 121°$ C. which is sufficient to form a press fit on a connection point, and from which a ring or loop of a diameter of down to 60 mm may be formed without kinking, while the second material contains at least one polymer, wherein said second material during high temperature sterilisation at 121° C. has a tendency to flow under the connection pressure arising during formation of a press fit and has a Shore A hardness of $\leq 65$, such that first plastic material is dimensionally stable at temperatures of $\geq 121°$ C. and the second plastic material is no longer dimensionally stable, and wherein said first plastic material is selected from the group consisting of styrene/ethylene/butylene rubber with PP, PIP with PP, SEPS with PP, or PP and SIS with PP, and wherein said second plastic material is selected from the group consisting of SEBS, SEPS or PE-copolymer.

* * * * *